United States Patent
Giovanniello

(10) Patent No.: US 10,590,284 B2
(45) Date of Patent: *Mar. 17, 2020

(54) FORMULA AND PROCESS FOR CROSSLINKING ANTIMICROBIALS TO SURFACES AND POLYMERS

(71) Applicant: Sanit Technologies LLC, Sarasota, FL (US)

(72) Inventor: Joseph Giovanniello, Wayne, NJ (US)

(73) Assignee: SANIT TECHNOLOGIES LLC, Sarasota, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/914,766

(22) PCT Filed: Aug. 29, 2014

(86) PCT No.: PCT/US2014/053475
§ 371 (c)(1),
(2) Date: Feb. 26, 2016

(87) PCT Pub. No.: WO2015/031790
PCT Pub. Date: Mar. 5, 2015

(65) Prior Publication Data
US 2016/0200918 A1    Jul. 14, 2016

Related U.S. Application Data

(60) Provisional application No. 61/871,887, filed on Aug. 30, 2013.

(51) Int. Cl.
*C09D 5/14* (2006.01)
*A01N 33/12* (2006.01)
(Continued)

(52) U.S. Cl.
CPC ............... *C09D 5/14* (2013.01); *A01N 33/12* (2013.01); *A01N 55/00* (2013.01); *B05D 1/007* (2013.01)

(58) Field of Classification Search
CPC ........ A01N 33/12; A01N 25/06; A01N 25/24; A01N 55/00; B05D 1/007; C09D 5/14
See application file for complete search history.

(56) References Cited

U.S. PATENT DOCUMENTS

| 6,604,531 B2 | 8/2003 | Nakamura et al. |
| 8,754,146 B2 | 6/2014 | Ziolkowski et al. |

(Continued)

FOREIGN PATENT DOCUMENTS

| JP | 2012001466 A | 1/2012 |
| JP | 2013501742 A | 1/2013 |

(Continued)

OTHER PUBLICATIONS

"Hurricane ES". Curtis Dyna Fog. Retrieved from http://www.dynafog.com/products/sanitationandgreenhouse/Hurricane-es/.*
(Continued)

*Primary Examiner* — Jose Hernandez-Diaz
(74) *Attorney, Agent, or Firm* — Michael Best & Friedrich LLP

(57) ABSTRACT

A process is described herein for applying antimicrobials to substrates to prevent the growth of biological agents. An antimicrobial-binder mixture is provided. The binder comprises guar gum, ammonium sulfate, urea, and methyl acryloid. The antimicrobial is an organo silane quarternary amine antimicrobial. The antimicrobial-binder mixture is ionized to comprise negatively charged particles. The antimicrobial-binder mixture is aerosolized to form fog. The fog is administered to the surface and dried.

8 Claims, 1 Drawing Sheet

101: Prepare binder

102: Mix antimicrobial with binder

103: ionize and aerosolize antimicrobial-binder mixture

104: apply antimicrobial-binder mixture to surface by fogging

105: dry antimicrobial-binder mixture

(51) Int. Cl.
  *B05D 1/00*  (2006.01)
  *A01N 55/00*  (2006.01)

(56) References Cited

U.S. PATENT DOCUMENTS

| | | | | |
|---|---|---|---|---|
| 2006/0182788 A1* | 8/2006 | Singh | ................... | A61K 47/32 424/448 |
| 2007/0241306 A1* | 10/2007 | Wehner | ................... | A61Q 5/02 252/67 |
| 2012/0258157 A1* | 10/2012 | Koltzenburg | .......... | A01N 33/12 424/409 |
| 2014/0120145 A1 | 5/2014 | Giovanniello | | |

FOREIGN PATENT DOCUMENTS

| | | | | |
|---|---|---|---|---|
| WO | 2006081497 A2 | 8/2006 | | |
| WO | WO 2011008204 A1 * | 1/2011 | .......... | D06M 13/432 |
| WO | WO 2011150103 A2 * | 12/2011 | ............. | C03C 17/30 |
| WO | 2013047642 A1 | 4/2013 | | |

OTHER PUBLICATIONS

"The Hurricane ES . . . the All New Portable Electrostatic Sprayer by Curtis Dyna-Fog Takes Ultra-Low-Volume and Low Volume Spraying to the Next Level" (2011) (hereafter "HurricaneES"), retrieved from https://www.pr.com/press-release/368441 (Year: 2011).*

Wikipedia, "Tourmaline", website [online], Wikipedia, 2014 [retrieved on Oct. 21, 2014]; retrieved from the Internet: <URL:http://en.wikipedia.org/wiki/Tourmaline>.

Dyna-Fog(R) Hurricane, "Cold Fog" ULV/Mister, Instruction Manual for Operation, Service, and Maintenance, Jan. 1, 2011, pp. 1-15.

European Patent Office Action for Application No. 14839717.7 dated Mar. 19, 2019 (3 pages).

Mexican Patent Office Action for Application No. MX/a/2016/002518 dated Oct. 8, 2019 (7 pages, partial English translation included).

* cited by examiner

101: Prepare binder

↓

102: Mix antimicrobial with binder

↓

103: ionize and aerosolize antimicrobial-binder mixture

↓

104: apply antimicrobial-binder mixture to surface by fogging

↓

105: dry antimicrobial-binder mixture

FORMULA AND PROCESS FOR CROSSLINKING ANTIMICROBIALS TO SURFACES AND POLYMERS

RELATED APPLICATIONS

This application claims priority to U.S. Provisional Application No. 61/871,887, filed Aug. 30, 2013.

BACKGROUND

Surfaces are hotbeds of microorganism activity. Serious illnesses, such as influenza, are easily spread by simple human touch. Common objects in public spaces, such as shared telephones and keyboards in offices, railings and seats in public transportation, check out touch screens at the supermarket, and even doorknobs, can all harbor dangerous viruses and bacteria. Harmful microorganisms may also be found on standard surfaces in American homes. For example, kitchens may harbor dangerous bacteria like *Escherichia coli* (a.k.a. "*E. Coli*"), *Camphylobacter*, and *Salmonella*, which can lead to food based illnesses such as food poisoning. Touch surfaces such as countertops and faucet, refrigerator, and cabinet handles are common breeding grounds for microbes.

While conventional disinfectant sprays and wipes kill some of these microorganisms, they do not prevent additional microorganisms from infecting these same areas shortly after cleaning. As a result, these surfaces need to be continually wiped down in order to prevent continuing microbe growth. Further, because traditional disinfectants work by poisoning infectious agents, it is possible for those agents to develop resistance to the treatment. This can result in the creation of a more dangerous infectious agent than the one originally targeted for destruction. One famous example of these types of resistant, dangerous microorganisms is the bacteria methicillin-resistant *Staphylococcus aureus*, commonly known as MRSA. Indeed, traditional treatments are not always effective against so-called "superbugs" like MRSA.

There is a significant need for an improved treatment for surfaces and other solid and porous substrates in order to prevent the spread of unhealthy microorganisms. There is further a need for such treatment to destroy infectious agents without risk of increasing resistance or creating resistant agents and to destroy dangerous resistant infectious agents that would not be destroyed with traditional treatments.

SUMMARY

In some embodiments described herein, a method of applying an antimicrobial to a surface to prevent biological agents from growing on that surface is presented. An antimicrobial-binder mixture is provided. The binder comprises guar gum, ammonium sulfate, urea, and methyl acryloid. The antimicrobial is an organo silane quarternary amine antimicrobial. The antimicrobial-binder mixture is ionized to comprise negatively charged particles. The antimicrobial-binder mixture is then aerosolized to form fog. The fog is administered to the surface and dried.

In another embodiment for applying an antimicrobial to a surface to prevent biological agents from growing on the surface, an antimicrobial-binder mixture is prepared. Water is heated to a temperature greater than 63° C. Guar gum is mixed with the water, and the mixture is cooled to a temperature between 57° C. and 63° C. The mixture is diluted, and ammonium sulfate and urea are mixed therewith before the mixture is diluted again. Methyl acryloid is the mixed therewith. The binder is mixed with an antimicrobial having the formula $NH_3C_{18}H_{36}R$ where R is a silane group, an ionizing agent, and water to form an antimicrobial-binder mixture. The binder comprises 2-3% of the antimicrobial-binder mixture by weight percent. The ionizing agent comprises 1% of the antimicrobial-binder mixture by weight percent. The antimicrobial comprises 2-3% of the antimicrobial binder mixture by weight percent. The mixture is ionized such that the mixture comprises negatively charged particles, and is aerosolized to form fog. The fog is administered the surface and dried at room temperature.

BRIEF DESCRIPTION OF THE DRAWINGS

FIG. 1 depicts a flow chart of a preferred embodiment of the methods described herein.

DETAILED DESCRIPTION

The disclosures herein relate to methods of applying antimicrobial agents to surfaces utilizing a binder. FIG. 1 provides a flow chart, describing one such embodiment. An aqueous binder solution may contain one or more components that form a binder to bind antimicrobials to substrates. One such aqueous binder solution that may be used with the methods described herein is comprised of guar gum. In some embodiments, the aqueous binder solution may further comprise ammonium sulfate, urea, and/or methyl acryloid. Examples of methyl acryloids that may be used in this binder include methyl methacrylate copolymers such as, for example, Dow Chemical's Paraloid® line of methyl methacrylate copolymers.

In one embodiment of an aqueous binder solution, the solution comprises approximately 1.5% guar gum by weight. In another embodiment of an aqueous binder solution, the aqueous binder solution may comprise 1.5% guar gum and approximately 2.0% ammonium sulfate by weight. In another embodiment of an aqueous binder solution, the solution may comprise approximately 1.5% guar gum, approximately 2.0% ammonium sulfate, approximately 0.9-1.0% urea, and approximately 1.75% methyl acryloid by weight.

A binder may be prepared for use in treating substrates, to include surfaces, according to the methods herein. (101) To prepare such a binder, approximately 102 pounds (approximately 46.3 kg) is heated to a temperature greater than 145° F. (63° C.). Approximately 3.5 lbs (1.59 kg) of guar gum is mixed with the water. Thereafter, the mixture is cooled to between approximately 135-145° F. (57-63° C.). Approximately 37.5 lbs (17 kg) of water is added to the mixture. The water is at a temperature less than or equal to 145° F. Approximately 4.5 lbs (2.04 kg) of ammonium sulfate is mixed therewith. After mixing the ammonium sulfate with the mixture, approximately 2 lbs (0.91 kg) of urea is mixed therewith. Once the mixing of the urea is complete, 75 lbs (34 kg) of water and 4 lbs (1.81 kg) of methyl acryloid is added to create a binder. This binder may then be used in methods to treat substrates, to include surfaces. One of skill in the art is aware that the weights of the binder components may be modified so long as the approximate proportions between those components are maintained.

To treat surfaces, an antimicrobial is mixed with the binder and water. (102) Such mixing may be done in any appropriate sized container to produce the amount of mixture desired for a job. In some embodiments, the container may be a mixing tank with an industrial mixer. One example of a mixer that may be used to mix the antimicrobial, binder, and water is the ¼ horsepower Hill Vortex mixer. As part of mixing the antimicrobial, binder, and water, the solution is mixed and heated to at least 100° F., and preferably to a temperature between 100° F. and 120° F. Preferably, the mixture is mixed for at least five minutes after reaching a temperature of at least 100° F. In some embodiments, a tank may include a heating element to streamline the heating process. One example of such a tank is a heated jacket style tank. One of skill in the art, however, appreciates that any appropriate heating element may be used.

The percentages of antimicrobial and binder used in this mixture are predetermined. In some embodiments, the weight percentage of antimicrobial is approximately 2% to 3%, and the weight percentage of the binder is approximately 2% to 3%.

Antimicrobials that may be used include organo silane quarternary amines capable of forming a spiked structure. Typically, these molecules are comprised of a silane group (R), a carbon chain ($C_xH_y$), and a quarternary amine ($NH_3$). The molecules are arranged such that the silane group is attached to one end of the carbon chain, while the amine is attached to the other end of the carbon chain, forming a molecular spike ($NH_3C_xH_yR$). One example of an organo silane quarternary amine that may be used is $NH_3C_{18}H_{36}R$. In a preferred embodiment, the antimicrobial is the Nelsperse Ultimate Protection antimicrobial agent, sold by Nelcon, Inc. in Paterson, N.J. In other embodiments, the organo silane quaternary amine antimicrobial may be Aegis Environmental Management's Dow Corning 5700 (3-(trimethoxysilyl)-propyldidecylmethyl ammonium chloride). Other embodiments may utilize organo silane quarternary amine antimicrobials such as $(CH_3O)_3Si(CH_2)_3N^+(CH_3)_2C_{18}H_{37}Cl^-$, $(CH_3O)_3Si(CH_2)_3N^+(C_2H_5)_3Cl^-$; $(CH_3O)_3Si(CH_2)_3N^+(CH_3)_2C_{18}H_{37}Br^-$; $(CH_3O)_3Si(CH_2)_3N^-(CH_3)_3Cl^-$; $(CH_3O)_3Si(CH_2)_3N^+(CH_3)_2CH_2C_6H_5Cl^-$; $(C_2H_5O)_3Si(CH_2)_3N^+(CH_3)_2C_{18}H_{37}Cl^-$; and $(CH_3O)_3Si(CH_2)_3N^+(CH_3)_2C_4H_9Cl^-$.

The quarternary amine structure of the molecular functions as the point of the spike. When this structure comes into contact with a cellular membrane, it pierces the same. The puncturing in the membrane brings about destruction of nutrient transport systems and structural integrity, leading to cell death. Of note, the amine point does not operate by poisoning the cells it comes into contact with. Rather, the amine point physically punctures the membranes of such cells.

In some embodiments, the antimicrobial-binder solution further includes an ionizing agent. It is hypothesized that the ionizing agent works to enhance the antimicrobial's ability to destroy harmful biological agents. The ionizing agent may also aid in ionizing the antimicrobial-binder mixture for fogging applications (discussed below). The ionizing agent may be mixed with the mixture. In one embodiment, the ionizing agent is tourmaline. One source of tourmaline that may be used in the antimicrobial-binder solution described herein is white ion powder at a particle size of 0.03 microns sold by Ion Trading Universal Co. in Tokyo, Japan. Other examples of ionizing agents include gray ion powder sold by Ion Trading Universal Co. in Tokyo, Japan; Shanghai Huzheng Nano Technology Co., Ltd.'s negative ion powder (available at hznano.en.alibaba.com/product/516339676-213716786/Negative_ion_powder.html); DB Chemic's Ion Powder (available at www.dbchemic.com/product/Ion.php); Root's Negative Ion Powder, Type C (available at www-.root-cn.com/Negative-Ion-Powder-Type-C.html); and Ion Trading's White Tourmaline Powder (available at www.n-ion.com/e/product/tourmaline-stones-powder/tpd-1-I.html). Other examples of ionizing agents include gadolinium, phosphorus, samarium, ytterbium, and neodymium. In a preferred embodiment, the ionizing agent comprises 1% of the antimicrobial-binder solution by weight percent.

After the antimicrobial and binder are mixed with water, the temperature of the mixture is adjusted to allow antimicrobial and binder to disperse within the water. In a preferred embodiment, the temperature is adjusted to one that permits even dispersion of the antimicrobial and binder within the water. Although this temperature will vary, in a preferred embodiment, the temperature is between approximately 37° C. (approximately 100° F.) and approximately 44° C. (approximately 110° F.).

A surface is chosen to receive the antimicrobial and binder mixture. Surfaces, generally, may include any non-fabric material. For example, polymers, glass, and metal may be surfaces. Surfaces may be rigid or flexible, and may be found in many different shapes and sizes. Surfaces may include solid substrates, porous substrates, and combinations thereof.

In some embodiments, the surface may undergo preparation steps prior to application of the antimicrobial and binder mixture. For example, a surface may be cleaned prior to the application. Cleaning may be helpful to remove potentially harmful materials that may exist on the surface. Cleaning may occur in a variety of ways. In some embodiments, cleaning occurs by treating the surface with, for example, ultraviolet light. In other embodiments, cleaning may include treatment with a commercially available cleansing product. For example, some of the test surfaces discussed in the examples below were cleaned with commercial antibacterial products Fantastic® and Formula 409® cleaners.

After the antimicrobial-binder mixture and surface are prepared, the antimicrobial-binder mixture is applied to the surface. Any method of applying a mixture to a surface may be utilized. Examples of such methods include, but are not limited to, fogging applications, dipping applications, and spraying applications. Preferably, the application method allows for even distribution of the antimicrobial-binder mixture to the surface. One application that permits even distribution is dipping. In an embodiment using dipping, the surface is submersed into the antimicrobial-binder mixture. In some embodiments, the submersion lasts for approximately one to two minutes.

A preferred embodiment is fogging. Fogging is preferred for several reasons, to include the ability to treat large surface areas in short amounts of time. For example, an entire room may be easily treated by utilizing the fogging methods described herein. Embodiments using fogging function by ionizing the antimicrobial-binder mixture. The mixture is ionized in the fogging machine so that the mixture comprises negatively charged ions. The negatively charged antimicrobial-binder mixture is further aerosolized by the fogging machine. One such fogging machine that can be utilized to practice the fogging portion of the methods described herein is the Hurricane Electric Portable Aerosol Applicator, which is available at www.dynafog.com/ulv/ecf/hurricane. The Hurricane may perform the functions of ionizing the antimicrobial-binder mixture so that the mixture is comprised of negative ions and forming aerosol particles ranging from approximately 5-50 microns. In an embodiment using fogging, the surface is exposed to fog from the fogging machine. In some embodiments, the exposure time is between six and ten seconds. In other embodiments, fogging may be utilized for a period of several minutes. The negatively charged fog comprised of the antimicrobial-binder mixture exits the fogging machine and enters the atmosphere. From there, it is attracted to the surfaces in the vicinity. This is due to positive surfaces carrying a positive charge. The electrical attraction holds the antimicrobial-binder mixture particles to the surface until drying is complete, at which point the binder ensures the mixture remains attached to the surface.

After application of the antimicrobial-binder mixture to the surface, the mixture is dried onto the surface. In a preferred embodiment, drying occurs at room temperature without excess air movement. As used herein, room temperature refers to temperatures between 20° C. and 26° C. (68° F.-79° F.). Drying time may be accelerated in some embodiments through use of a blower or fan to increase air movement, or through the use of heat.

Upon completion of the drying process, the surface is chemically bound to the dried binder and antimicrobial. The antimicrobial and binder are present on the surface at approximately a 1:1 ratio by weight. The binder binds the surface to the antimicrobial, such that the antimicrobial is oriented in a spike structure that is exposed on the outer sides of the surface surface. The quarternary amine portion of the spike structure is oriented distal to the treated surface, with the quarternary amine forming the peak of the spike, while the silane group is oriented proximate the surface, so as to form a silane bond with the same. Due to those chemical bonds, the antimicrobial remains fixed to the surface.

Experimental Results

Testing Against MRSA

Surfaces were treated pursuant to the methods described herein and tested to determine their effectiveness against infectious agents. Polycarbonate coupons were treated with the antimicrobial-binder mixtures disclosed herein. The coupons were placed on a planar surface six feet from a fogging unit. The antimicrobial-binder mixture was then applied by fogging for three to four minutes, and drying for ten to twenty minutes. Drying was performed by air drying at a temperature of approximately 36° C.

Another set of coupons were treated such that they contained a biofilm coating. The biofilm coating comprised Methicillin Resistant *Staphylococcus aureus* ("MRCA"). The biofilm coated coupons were exposed to the coupons treated pursuant to the methods disclosed herein. After eight hours of exposure, colony morphology and gram stain indicated that no MRSA organisms remained. Tests performed after twenty four hours of exposure returned similar results. These results are consistent with eradicating the MRSA organisms in the biofilm.

Testing in Hospital Settings

Using the methods described herein, antimicrobials were applied to hard surfaces in hospitals. Over a six week period, the surfaces were tested to determine whether there was a recurrence of biological agents. The results are shown in Table 1 below. The measurements taken on February 25 were taken prior to application of the antimicrobial to the surfaces. Thereafter, a single application occurred. Measurements were then taken on March 12, March 30, and April 14. As seen, after treatment, biological agents were dramatically reduced and such reduced levels persisted through the end of testing. These results indicate that application of the antimicrobials via the methods described herein not only destroyed biological agents that existed on the surfaces at the time of treatment, but also continued to keep those surfaces relatively free of new biological agents for weeks afterwards.

TABLE 1

Testing results showing decrease in biological agents after application of

| Item Treated | Organisms on February 25 | Organisms on March 12 | Organisms on March 30 | Organisms on April 14 |
|---|---|---|---|---|
| Bed Rail | 490 | <10 | <10 | <10 |
| Sink Counter | 190,000 | <10 | <10 | <10 |
| Windowsill | 260 | <10 | <10 | <10 |
| Chart Holder | 340 | <10 | <10 | <10 |
| Bed Tray | 2,900 | <10 | <10 | <10 |
| Closet Handle | 230 | <10 | <10 | <10 |

Testing Against Common Household Micro-Organisms.

Tests were performed on kitchen garbage cans obtained from American households. Tests demonstrated that application of the antimicrobial-binder solutions described herein via the methods of the specification effectively killed common household microorganisms.

These tests were performed using the SystemSURE Plus™ ATP Hygiene/Sanitation Monitoring System. The SystemSURE Plus™ detects adenosine tri-phosphate ("ATP") indicative of microorganism growth and contamination. Test swabs were used to swab the rims of the subject kitchen trash can. Swabbing was done over a 4"×4" square while rotating the swab. The swab was then placed in a test tube and mixed with a liquid testing reagent provided as part of the SystemSURE Plus™ testing kit. This reagent includes, at least in part, the enzymes luciferin/luciferase, which react with any ATP present in the sample swab to emit light. The emitted light is then measured by the SystemSURE Plus™ device. There is a direct correlation between the amount of ATP present in a sample and the amount of light emitted. In particular, every 1 femtomole of ATP emits 1 Relative Light Unit of light. Thus, it is possible to measure the amount of ATP present in a sample.

Two test swabs were taken from the rim of garbage cans prior to treatment pursuant to the SystemSURE Plus™ System. The SystemSURE Plus™ System returned readings indicating 1450 femtomoles of ATP, indicating the presence of microorganisms. Utilizing the methods described herein, the garbage cans were fogged for several seconds with an antimicrobial-binder solution that included an ionizing agent. After drying, two additional test swabs were taken from the garbage cans and tested using the SystemSURE Plus™ System, which returned readings indicating zero femtomoles of ATP were present. These results indicate that treatment via the methods described herein destroys common household microorganisms.

Using a similar luminometer kit, tests were also performed on toilets to measure ATP. Several samples were taken. The first sample was taken on toilet bowl without any cleaning. The data returned by the luminometer indicated bacterial growth in excess of 3000. Thereafter, the toilet was washed with "Kaboom" toilet bowl cleaner and a second sample was taken. This sample indicated a bacterial count of 340, indicating that cleaning alone did not destroy all bacterial growth.

The toilet bowl was then treated according to the methods described herein. After this application, the bacterial count was lowered to 19. A follow up sample was taken two weeks later, returning a count of 34. These experiments demonstrate that the methods in the instant application result in greater destruction of biological agents than traditional cleaning methodology. They also come with the benefit of extended protection over, at least, weeks.

Although the present methods, compositions, and surfaces have been shown and described in considerable detail with respect to only a few/particular exemplary embodiments thereof, it should be understood by those skilled in the art that it is not intended to limit the methods, compositions, or surfaces to the embodiments since various modifications, omissions, and additions may be made to the disclosed embodiments without materially departing from the novel teachings and advantages described herein, particularly in light of the foregoing teachings.

What is claimed is:

1. A method of preventing biological agents from growing on a surface by applying an antimicrobial to the surface, comprising:
    providing an antimicrobial-binder mixture, wherein the binder comprises guar gum, ammonium sulfate, urea, and a methyl methacrylate copolymer, and wherein the antimicrobial is an organo silane quarternary amine antimicrobial;
    aerosolizing the antimicrobial-binder mixture to form fog;
    administering the antimicrobial-binder fog to the surface; and
    drying the antimicrobial-binder mixture on the surface.

2. The method of claim 1, wherein providing the antimicrobial-binder mixture further comprises:
    preparing a binder solution, wherein the binder solution is characterized by comprising approximately 1.5% guar gum by weight, approximately 2% ammonium sulfate by weight, approximately 0.9-1.0 urea by weight, and approximately 1.75% methyl acryloid by weight; and
    mixing the binder solution with the antimicrobial.

3. The method of claim 1, further comprising cleaning the surface prior to administering the antimicrobial-binder mixture to the surface.

4. The method of claim 3, wherein cleaning comprises treating the surface with ultraviolet light.

5. The method of claim 1, wherein drying occurs at room temperature.

6. A method of preventing biological agents from growing on a surface by applying an antimicrobial to the surface, comprising:
    preparing an antimicrobial-binder mixture by:
        heating water to a temperature greater than 63° C.;
        mixing guar gum with the water to form a first mixture;
        cooling the first mixture to a temperature between 57° C. and 63° C.;
        diluting the first mixture;
        mixing ammonium sulfate and urea with the first mixture to form a second mixture;
        diluting the second mixture;
        mixing a methyl methacrylate copolymer with the second mixture to form a binder; and
        mixing the binder, an antimicrobial having the formula $NH_3C_{18}H_{36}R$ where R is a silane group, and water to form an antimicrobial-binder mixture, wherein the binder comprises 2-3% of the antimicrobial-binder mixture by weight percent, and the antimicrobial comprises 2-3% of the antimicrobial binder mixture by weight percent;
    aerosolizing the antimicrobial-binder mixture to form fog;
    administering the antimicrobial-binder fog to the surface; and
    drying the antimicrobial-binder mixture on the surface at room temperature.

7. A method of preventing biological agents from growing on a surface by applying an antimicrobial to the surface, comprising:
    providing an antimicrobial-binder mixture, wherein the binder comprises guar gum, ammonium sulfate, urea, and a methyl methacrylate copolymer, and wherein the antimicrobial with the formula $NH_3C_{18}H_{36}R$ where R is a silane group;
    aerosolizing the antimicrobial-binder mixture to form fog;
    administering the antimicrobial-binder fog to the surface; and
    drying the antimicrobial-binder mixture on the surface.

8. A method of preventing biological agents from growing on a surface by applying an antimicrobial to the surface, comprising:
    preparing an antimicrobial-binder mixture by:
        heating water to a temperature greater than 63° C.;
        mixing guar gum with the water to form a first mixture;
        cooling the first mixture to a temperature between 57° C. and 63° C.;
        diluting the first mixture;
        mixing ammonium sulfate and urea with the first mixture to form a second mixture;
        diluting the second mixture;
        mixing a methyl methacrylate copolymer with the second mixture to form a binder; and
        mixing the binder, an organo silane quarternary amine antimicrobial, and water to form an antimicrobial-binder mixture, wherein the binder comprises 2-3% of the antimicrobial-binder mixture by weight percent, and the antimicrobial comprises 2-3% of the antimicrobial binder mixture by weight percent;
    aerosolizing the antimicrobial-binder mixture to form fog;
    administering the antimicrobial-binder fog to the surface; and
    drying the antimicrobial-binder mixture on the surface at room temperature.

* * * * *